United States Patent [19]

Naylor

[11] 4,454,074
[45] Jun. 12, 1984

[54] SALTS OF DICYCLOPENTADIENE SULFONATE AND METHOD OF PREPARING

[75] Inventor: Carter G. Naylor, Austin, Tex.

[73] Assignee: Texaco Inc., White Plains, N.Y.

[21] Appl. No.: 420,203

[22] Filed: Sep. 20, 1982

[51] Int. Cl.$^3$ .................... C07C 143/20; C07C 143/22
[52] U.S. Cl. ................................ 260/503; 252/8.55 D
[58] Field of Search ........................................ 260/503

[56] References Cited

U.S. PATENT DOCUMENTS

| | | | |
|---|---|---|---|
| 2,921,958 | 1/1960 | Feichtinger | 260/503 |
| 3,370,080 | 2/1968 | Block et al. | 260/457 |
| 3,764,569 | 10/1973 | Ali et al. | 252/554 |
| 4,070,396 | 1/1978 | Convers et al. | 260/513 |
| 4,087,457 | 5/1978 | Convers et al. | 260/513 |
| 4,267,123 | 5/1981 | Chen et al. | 260/501.12 |
| 4,275,013 | 6/1981 | Tokosh et al. | 260/504 |

OTHER PUBLICATIONS

Shepherd et al., Chem. Abst., 82, 85, 815 k (1975).
R. Morrison and R. Boyd, Organic Chemistry, Allyn and Bacon Inc., Boston (3rd Ed. 1973) p. 953.

*Primary Examiner*—Nicky Chan
*Attorney, Agent, or Firm*—Robert A. Kulason; Jack H. Park; Harold J. Delhommer

[57] ABSTRACT

A novel series of compounds is disclosed which comprises salts of dicyclopentadiene sulfonate. Methods for producing these compounds by bisulfite addition and for controlling the proportion of monosulfonates and disulfonates in the product are also disclosed.

8 Claims, No Drawings

SALTS OF DICYCLOPENTADIENE SULFONATE AND METHOD OF PREPARING

FIELD OF THE INVENTION

The present invention concerns a novel group of sulfonate compounds and their method of preparation. More particularly, the novel compounds are alkali metal salts, ammonium salts or amine salts of dicyclopentadiene sulfonate.

PRIOR ART

It is well known in the art that sulfonates can be prepared by adding bisulfite to an olefin in a liquid reaction medium. Numerous organic sulfates and sulfonates have also been reported in the literature, particularly in the areas of detergent and oil recovery uses.

U.S. Pat. No. 3,370,080 discloses the preparation of bicycloalkane sulfates and sulfonates having at least two alkyl side chains. The patent advocates reacting a monoolefin with a conjugated cyclodiolefin in a thermal condensation reaction at temperatures of about 175° to 200° C.

U.S. Pat. Nos. 4,070,396; 4,087,457; 4,267,123 and 4,275,013 all disclose the preparation of organic sulfonates through bisulfite addition to olefins or alkenes. U.S. Pat. Nos. 4,070,396 and 4,087,457 describe methods for increasing the reaction rate of higher molecular weight olefins in the formation of alkane sulfonates through bisulfite reactions. Both references concern only the use of non-alpha olefins having 12 or more carbon atoms. Another method of preparation of alkane sulfonates is disclosed in U.S. Pat. No. 4,275,013. The described process is limited to alpha olefins as starting reactants. The use of bisulfite reactions to produce propane sulfonates from non-olefinic reagents is described in U.S. Pat. No. 4,267,123. The final products of the U.S. Pat. No. 4,267,123 method are propane sulfonates or aryl compounds with propane sulfonate side chains.

The dimerization reaction of cyclopentadiene to form dicyclopentadiene is disclosed in R. Morrison and R. Boyd, *Organic Chemistry*, Allyn and Bacon, Boston (3rd ed. 1973) p. 953.

SUMMARY OF THE INVENTION

The present invention is a novel series of compounds which comprise salts of dicyclopentadiene sulfonate and a method for producing these compounds from the basic reactants of dicyclopentadiene and alkali metal bisulfite or ammonium bisulfite. These compounds may be monosulfonates, disulfonates or sulfinate-sulfonates of dicyclopentadiene.

The preferred method for preparing the novel dicyclopentadiene sulfonate salts involves adding and mixing a low molecular weight alkanol and an alkali metal hydroxide or ammonium hydroxide to dicyclopentadiene with water. Finally, bisulfite is added and mixed to the reaction mixture along with oxygen.

DETAILED DESCRIPTION

The dicyclopentadiene sulfonate compounds of the present invention have the general formula:

$$DH_{x-y}(SO_3M)_x(SO_2M)_y,$$

where M is an alkali metal or ammonium cation with a valence of +1, and $$DH_{x-y}(SO_3)_xM_{x/2}(SO_2)_yM_{y/2},$$

where M is an alkaline-earth metal cation with a valence of +2. In both formulas, D is a tricyclic ring structure of $C_{10}H_{12}$ derived from the Diels-Alder dimer of cyclopentadiene, x is 1 or 2, and y is 0, 1 or 2, provided that y is equal to or less than x. The preferred alkali metal cations are sodium and potassium ions and the preferred alkaline-earth metal cations are calcium and magnesium ions. According to IUPAC systematic rules, dicyclopentadiene should be named 3a,4,7,7a-tetrahydro-4,7-methanoindene.

The especially preferred method of making these compounds yields both monosulfonate salts and disulfonate salts of dicyclopentadiene. The monosulfonate salts are believed to be a mixture of two compounds having the following structures:

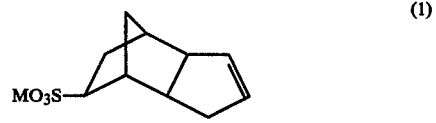

(1)

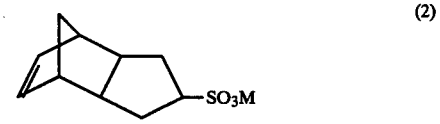

(2)

It is presently believed that the first structure (1) is the predominate structure. However, it represents numerous positional and optical isomers, all of which may be present in the compounds prepared according to the invention. Likewise, structure (2) represents several possible isomers. Structure (1) illustrates the sulfonate group attached to the norbornyl ring.

Disulfonate salts of dicyclopentadiene are also prepared concurrently with the monosulfonate salts when the present method is performed. One possible structure of several positional and optical isomers is:

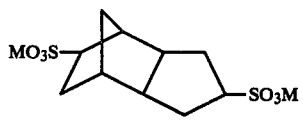

In addition to monosulfonate and disulfonate salts, sulfinate-sulfonate salts may also be present. In such an instance, the sulfinate groups are adjacent to the sulfonate groups. One possible structure is:

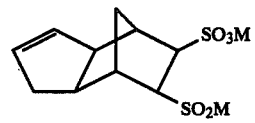

The novel dicyclopentadiene sulfonate salts are very useful in enhanced oil recovery and corrosion control. The sweep efficiency is equal or superior to the present art, and the cost of these compounds is less than the cost of sulfonates presenty used in enhanced oil recovery. The compounds of the invention are also quite successful in controlling hydrogen sulfide corrosion when used as an additive in corrosion treating solutions.

The dicyclopentadiene sulfonate molecule differs from most sulfonates and sulfates used in enhanced oil recovery by molecular weight and structure. The equivalent weight of the sodium salt of dicyclopentadiene sulfonate is 236 grams per mole, while the equivalent weight of most prior art sulfonates is in the 350–700 grams per mole range. Second, sulfonate molecules employed in oil recovery generally have an 8 to 16 carbon chain attached to an aromatic structure to serve as the hydrophobic portion of the surfactant molecule. Sulfonated dicyclopentadiene has only a compact dicyclopentadiene group to serve as the hydrophobic portion of the molecule. Because of these differences in molecular structure and equivalent weight, one would not expect the salts of dicyclopentadiene sulfonate to function efficiently in an enhanced oil recovery surfactant systems.

Dicyclopentadiene is the Diels-Alder dimer of 1,3-cyclopentadiene, a component of $C_5$ streams of ethylene manufacturing plants. The dimerization reaction occurs spontaneously within the temperature range of 0°–170° C. Above 170° C., the dimer reverts to monomer cyclopentadiene. When separated from ethylene plant $C_5$ streams, dicyclopentadiene is frequently contaminated with other $C_{10}$ to $C_{12}$ cyclic olefins that are difficult to separate out. However, the method of the present invention may be practiced with dicyclopentadiene that is from about 50% to 100% pure. Thus, hydrocarbon streams rich in dicyclopentadiene may be used to practice the method of the invention.

The preferred method of making the novel dicyclopentadiene sulfonate salts is by bisulfite addition to dicyclopentadiene. Dicyclopentadiene is placed in a reaction medium of alcohol and water and a small quantity of hydroxide is added. The pH of the reaction mixture is then adjusted to a predetermined pH, preferably between about 5.5 and about 8.0, and the mixture is heated to about 30° to about 70° C., preferably 55° C. Bisulfite is then slowly added to the reaction mixture at such a rate as to maintain the preselected pH while concurrently adding oxygen to the reaction mixture. Bisulfite addition should be slow and occur over a period of about 1 to about 24 hours, preferably about 1 to about 8 hours.

After bisulfite addition has been terminated, the alcoholic solvent is removed by distillation and replaced with water. The dicyclopentadiene sulfonate salts are then available for use in an aqueous solution. Alternatively, the dicyclopentadiene sulfonate salts may be removed from solution by filtration.

It is preferred that a small quantity of an alkali metal hydroxide or ammonium hydroxide be added to the aqueous alcohol medium prior to adjusting the pH of the reaction mixture. The hydroxide added should have the same cation as the cation of the desired dicyclopentadiene sulfonate salt. Sodium hydroxide and ammonium hydroxide are the preferred hydroxide additives just as the sodium and ammonium salts of dicyclopentadiene sulfonate are the preferred products.

It is recommended that the alkanol employed to create the aqueous alcoholic reaction medium be a low molecular weight alcohol such as methanol, ethanol, propanol, isopropanol, butanol or isobutanol. Isopropanol is especially preferred.

The bisulfite added to the reaction mixture is selected from the group consisting of sodium bisulfite, potassium bisulfite, calcium bisulfite, magnesium bisulfite or ammonium bisulfite. The bisulfite added supplies the cation of the desired dicyclopentadiene sulfonate salt. The concurrent addition of oxygen or air provides oxygen for the initiation of the bisulfite reaction. Bubbling oxygen through the reaction medium is the preferred means of addition. The rate of flow of the air or oxygen added is not critical to the process.

It is also been unexpectedly discovered that the pH at which the bisulfite reaction takes place is critical to the proportion of monosulfonates and disulfonates in the final product. The proportion of monosulfonates to disulfonates changes considerably at different reaction medium pHs within the suggested pH range of about 5.5 to about 8.0 for the bisulfite reaction. For example, bisulfite reaction conducted according to the process of the invention at a pH of about 7.2 yields about 80% to 85% monosulfonates in the final product. But when the reaction pH is changed to about 6.0, the percentage of monosulfonates drops to about 15% to about 20% and the percentage of disulfonate increases to about 50% of the dicyclopentadiene sulfonate molecules produced.

The following examples will further illustrate the novel dicyclopentadiene sulfonate compounds and the inventive method of producing them. These examples are given by way of illustration and not as limitations on the scope of the invention. Thus, it should be understood that reactants and reaction conditions may be varied with the compounds produced and the methods of production still remaining within the scope of the invention.

EXAMPLE I

A one-liter three-neck flask was charged with 100 grams of dicyclopentadiene (95% grade), 200 grams of isopropyl alcohol, 100 grams of water and 14 grams of 20% sodium hydroxide. A 33.3 weight percent sodium bisulfite ($Na_2S_2O_5$) aqueous solution was added to adjust the pH to 7.2. After heating the reaction mixture to 55° C., air was bubbled in at 30 milliliters per minute. Concurrently, sodium bisulfite was slowly added at a rate sufficient to maintain the pH of the reaction mixture at 7.2. After 288 grams of the 33.3 weight percent sodium bisulfite solution had been added, uptake ceased. Elapsed time of bisulfite addition was 7.75 hours.

The isopropanol solvent was removed by distillation and replaced with water. Quantitative analysis by acid resin titration showed 817 milliequivalents of sulfonate in the product, indicating that some disulfonate was formed in addition to monosulfonate dicyclopentadiene. 817 milliequivalents was a 114% yield over the 720 milliequivalents of dicyclopentadiene originally charged to the flask.

EXAMPLE 2

The procedure of Example 1 was followed except for a change in reaction pH to 6.5 and a shortening of bisulfite reaction time to 2.3 hours. Titration analysis indicated a 92% sulfonate yield.

EXAMPLE 3

The procedure of Example 1 was followed except for a change in reaction temperature to 35° C. and a shortening of bisulfite reaction time to 4.9 hours. Analysis indicated a sulfonate yield of 93%.

EXAMPLES 4–7

The procedure of Example 1 was followed again except that the reaction mixture was maintained at different pH levels and bisulfite reaction times were changed. The impact of reaction pH on total sulfonate yield and product distribution is strikingly shown by the data of Examples 4–7 in Table I. As pH is lowered, bisulfite incorporation is greatly increased. Isotachophoresis chromatography (ITPC) was used to approximate product distribution by type of ionic charge. These results were approximated and not calibrated to mole fraction or weight fraction. Clearly, the proportion of diionic and higher ionic products increased at the expense of monosulfonate products as the pH was decreased. Thus, a lower bisulfite reaction pH clearly favors dicyclopentadiene disulfonate formation. It is known from other work that sulfinate formation is also favored by a lower pH.

TABLE I

| Example | pH | Time, hr. | Yield % | ITPC Zone Length Ratio (2 ml of 1% soln.) | | |
|---|---|---|---|---|---|---|
| | | | | Mono-ionic | Di-ionic | Higher ionic |
| 4 | 7.2 | 8.0 | 105 | 84 | 16 | 0 |
| 5 | 6.8 | 6.8 | 119 | 56 | 30 | 14 |
| 6 | 6.4 | 7.0 | 175 | 34 | 45 | 21 |
| 7 | 6.0 | 6.3 | 241 | 19 | 46 | 35 |

EXAMPLE 8

The ammonium salt of dicyclopentadiene sulfonate was created by charging the one liter flask with 100 grams of dicyclopentadiene, 200 grams of isopropanol, 100 grams of water and 1 gram of concentrated ammonium hydroxide. A 44% by weight aqueous solution of ammonium bisulfite was added to the reaction mixture at a 7.5 pH with an air flow rate of 30 milliliters per minute and a reaction temperature of 55° C.

474 grams of ammonium bisulfite was added over 19.5 hours. Isopropanol was then stripped from the product by distillation and the product diluted with water. 1096 grams of product was recovered. Titration analysis indicated 1283 milliequivalents of sulfonate which was a 170% yield from the dicyclopentadiene originally charged. This indicated an 85% sulfonation of all double bonds in the dicyclopentadiene. Thus, most of the product consisted of the ammonium salt of disulfonated dicyclopentadiene.

EXAMPLE 9

Sodium dicyclopentadiene sulfonate prepared at a pH of 7.0 was concentrated to give a 50% solution of sodium dicyclopentadiene sulfonate in water. On cooling, solids began to precipitate from solution. The solids were isolated by filtration and analyzed by isotachophoresis chromatography (ITPC) and NMR.

As indicated by Table II, the isolated solids were predominantly monosulfonates, but also included sulfonates of higher ionic types. Attemps to recrystallize the isolated solids proved unsuccessful. It is assumed that the large number of isomers in the monosulfonated dicyclopentadiene prevented recrystallization.

TABLE II

| Fraction | Wt. of solids, g | ITPC Zone Length Ratio | | | NMR, mole ratio |
|---|---|---|---|---|---|
| | | Mono- | Di- | Higher ionic | Mono:Di |
| Starting solution | 54 | 47% | 43% | 11% | — |
| Isolated solids | 12 | 75 | 21 | 4 | 67:33 |
| Mother liquor | | 44 | 45 | 11 | 53:47 |

Many other variations and modifications may be made in the concept described above by those skilled in the art without departing from the concept of the present invention. Accordingly, it should be clearly understood that the concepts disclosed in the description are illustrative only and are not intended as limitations on the scope of the invention.

What is claimed:

1. The compounds consisting of sulfonate or sulfonate-sulfinate salt derivatives of dicyclopentadiene, wherein said salts have a cation selected from the group consisting of alkaline-earth metal, alkali metal and ammonium ions.

2. The compounds of claim 1, wherein the compounds are monosulfonates.

3. The compounds of claim 1, wherein the compounds are disulfonates.

4. The compounds of claim 1, wherein the compounds are a mixture of monosulfonates and disulfonates.

5. A compound of the formula:

$DH_{x-y}(SO_3M)_x(SO_2M)_y$, wherein D is a tricyclic ring structure of $C_{10}H_{12}$ derived from the Diels-Alder dimer of cyclopentadiene, M is an alkali metal or ammonium cation, x is 1 or 2, and y is 0, 1 or 2, provided that y is equal to or less than x.

6. The compound of claim 5, wherein $(SO_3M)$ and $(SO_2M)$ are attached to a norbornyl ring of D.

7. A compound of the formula:

$DH_{x-y}(SO_3)_xM_{x/2}(SO_2)_yM_{y/2}$, wherein D is a tricyclic ring structure of $C_{10}H_{12}$ derived from the Diels-Alder dimer of cyclopentadiene, M is an alkaline-earth metal cation, x is 1 or 2, and y is 0, 1 or 2, provided that y is equal to or less than x.

8. The compound of claim 7, wherein $(SO_3)_xM$ and $(SO_2)_yM$ are attached to a norbornyl ring of D.

* * * * *